United States Patent [19]

Coulson et al.

[11] 4,034,076
[45] July 5, 1977

[54] PROCESS FOR MAKING TOOTHPASTE

[75] Inventors: James Coulson, Bracknell, England; Malcolm Richard Nearn, Ingleburn, Australia

[73] Assignee: Lever Brothers Company, New York, N.Y.

[22] Filed: Mar. 3, 1975

[21] Appl. No.: 554,880

[30] Foreign Application Priority Data

Mar. 7, 1974 United Kingdom ............ 10303/74

[52] U.S. Cl. ............................ 424/49; 252/387
[51] Int. Cl.² ...................................... A61K 7/16
[58] Field of Search ........................ 424/49–58; 252/387; 148/6.27

[56] References Cited

UNITED STATES PATENTS

| | | | |
|---|---|---|---|
| 1,912,175 | 5/1933 | Blough et al. | 252/387 |
| 3,506,499 | 4/1970 | Okada et al. | 148/6.2 |
| 3,678,155 | 7/1972 | Clippingdale et al. | 424/52 |

FOREIGN PATENTS OR APPLICATIONS

| | | | |
|---|---|---|---|
| 845,611 | 8/1960 | United Kingdom | 424/49 |
| 1,137,206 | 12/1968 | United Kingdom | 424/57 |

OTHER PUBLICATIONS

Mears et al., *Chemical Trade Journal and Chemical Engineer*, July 30, 1943, pp. 93 & 94.
Kirchgaessner, *Seifen. Cele. Fette. Wachse.*, vol. 98, pp. 383–392, 1972.

*Primary Examiner*—Lewis Gotts
*Assistant Examiner*—Cary Owens
*Attorney, Agent, or Firm*—Kenneth F. Dusyn; James J. Farrell; Melvin H. Kurtz

[57] ABSTRACT

This invention relates to a process for inhibiting the swelling of aluminium tubes containing toothpastes comprising alumina trihydrate, in which process there is incorporated in the toothpaste a silica sol of which the silica particles are negatively charged.

4 Claims, No Drawings

PROCESS FOR MAKING TOOTHPASTE

This invention relates to a process for making toothpastes.

In U.S. Pat. Nos. 3,678,155 and 3,662,060 it is disclosed that toothpastes containing as abrasive cleaning agents milled alumina trihydrates can give rise to the corrosion of aluminum toothpaste tubes even at neutral pH. Typical of such materials are those currently available from the British Aluminium Chemicals Limited under the designations BACO AF239, BACO AF240, BACO AF260 and BACO AF280, that available from Matinswerke GmbH under the designation "Tonerdehydrat N"and that available from Produits Chimiques Pechiney St. Gobain SA under the designation FB60; these materials have average particle sizes ranging from about 5 to about 16 microns. We have found that toothpastes made with such materials can swell on storage due to hydrogen gas production which arises from corrosive attack on the aluminium of the toothpaste tube in which they are packed. Serious swelling of toothpaste tubes makes them unsuitable for commerical sale.

Toothpaste manufacturers have therefore recognised that there is a need in the art to incorporate stabilisers in such toothpastes, ie materials which will reduce or prevent the incidence of tube swelling. In the two prior patent specifications referred to above there are disclosed two effective stabilisers.

It is an object of the present invention to provide another means of stabilising toothpastes containing these alumina trihydrates.

We have now found that the swelling of aluminium tubes due to hydrogen gas produced in the corrosive attack on the aluminium by toothpastes containing certain forms of alumina trihydrate can be inhibited by the incorporation into the toothpaste of a silica sol in which the silica particles are negatively charged. Suitable sols are those having a silica concentration of from 5 to 40% by weight.The amount of the sol incorporated in the tothpaste will usually be in the range 0.001% to 3% (although higher amounts can be used) calculated as silica by weight of the toothpaste. The sol will usually have a pH in the range 8 to 11.

The alumina trihydrate included in the toothpaste as an abrasive cleaning agent will have an average particle size (weight median diameter) in the range about 3 to about 30 microns and will usually be present in an amount of at least 20% by weight of the toothpaste and preferred amounts are from about 25 % to about 60 % by weight of the toothpaste. This abrasive grade of alumina trihydrate is produced commercially by the Bayer process in which hydrated alumina is precipitated in an average particle size of about 50 to 100 microns from a solution of sodium aluminate, washed, dried at a low temperature and then milled. An alumina trihydrate may be tested to determine whether it can lead to gassing of aluminium tubes, by making up a toothpaste according to the standard formula given hereinafter, packing the toothpaste in unlacquered aluminium tubes, and storing the toothpaste, preferably from 6 to 12 tubes of the toothpaste, for 3 months at 50° C. If any swelling due to hydrogen gas producton results, that alumina trihydrate is a corrosive form of alumina trihydrate.

Since toothpastes of marked acidity or alkalinity can corrode aluminium by reason of acid or alkaline attack of the aluminium, the pH of toothpastes of the invention should be in the range about 6 to about 8.

The stabilised toothpastes produced in accordance with the invention may be packed in unlacquered aluminium tubes. Should it be desired to pack the toothpaste in lacquered tubes the stabilising effect of the silica sol is nevertheless valuable since it is difficult in commercial practice to avoid the occurrence of slight imperfections in the lacquer coating.

The invention will now be illustrated by reference to the following experiments that have been carried out. Percentages are by weight.

The standard toothpaste referred to herein has the following formula:

|  | % |
| --- | --- |
| Milled alumina trihydrate | 55.00 |
| Sorbitol (70% syrup) | 27.00 |
| Sodium carboxymethylcellulose | 0.80 |
| Sodium lauryl sulphate | 1.50 |
| Titanium dioxide | 1.50 |
| Sodium saccharin | 0.20 |
| Benzoic acid | q.s.* |
| Flavour | 1.00 |
| Water | to 100.00 |

*to give a pH in the range 6.8 to 7.2

A toothpaste (Toothpaste A) was made according to the above standard formula using an alumina trihydrate sold under the trade name TONERDEHYDRAT N (by Martinswerke GmbH, Germany), which material had an average particle size of about 12 microns. The toothpaste was packed in unlacquered aluminium tubes and 6 tubes were stored at 50° C for 3 months. After this time all the toothpaste tubes were severly swollen due to hydrogen gas production and the crimped ends of the tubes were starting to be pushed open.

The above formula was modified in accordance with the following Examples of the invention.

EXAMPLES 1 TO 6

In the above formula was included an amount of the silica sol available under the trade named LUDOX SM-30 : it had a silica concentration of 30 % by weight and a pH of 9.5. The silica particles of the sol had a size of about 7 to 8 millimicrons and were negatively charged. The amount of water included in the toothpaste was correspondingly reduced. The silica sol was pre-mixed with the water, sorbitol syrup and other soluble ingredients prior to the addition of the insoluble ingredients.

6 tubes of the toothpaste were stored at 50° C for 3 months and the degree of swelling recorded. The results are indicated in the following Table.

Table

| Example | Amount of Silica Sol added (% by weight of the toothpaste) | Degree of Swelling |
| --- | --- | --- |
| 1 | 0.01 | Very slight swelling |
| 2 | 0.03 | Very slight swelling |
| 3 | 0.10 | Very slight swelling |
| 4 | 0.30 | No noticeable swelling |
| 5 | 1.00 | No noticeable swelling |
| 6 | 5.00 | No noticeable swelling |

The tests showed that the silica sol had a marked inhibitory effect on the gassing of the tubes on storage.

Another toothpaste (Toothpaste B) was made according to the above standard formula using an alumina trihydrate sold under the trade name BACO AF239 (by British Aluminium Chemicals Limited), which material had an average particle size of about 16 microns. The toothpaste was packed in unlacquered aluminium tubes and 6 tubes of the toothpaste were stored at 50° C for 3 months. After this time the tubes were considerably swollen, although the crimped ends of the tubes were still intact.

Toothpaste B was modified by including, in accordance with a further example of this invention, (Example 7), 0.1% of LUDOX SM-30 silica sol, which was incorporated in the same way as in the previous examples. When 6 tubes of the toothpaste of Example 7, packed in unlacquered aluminium tubes, were stored at 50° C for 3 months no swelling of any of the tubes was noticeable.

Another toothpaste (Toothpaste C) was made also using BACO AF239 alumina trihydrate according to the following formula:

|  | % |
|---|---|
| Milled alumina trihydrate | 50.00 |
| Sorbitol (70% syrup) | 27.00 |
| Xanthan gum | 1.20 |
| Sodium lauryl sulphate | 1.50 |
| Titanium dioxide | 1.50 |
| Sodium saccharin | 0.21 |
| Formalin | 0.05 |
| Benzoic acid | 0.27 |
| Sodium hydroxide | 0.01 |
| Flavour | 1.30 |
| Water | to 100.00 |
| pH = 6.8 | |

When this toothpaste was stored at 65° C for 1 month the toothpaste caused severe swelling of the aluminium tubes. This toothpaste was modified in accordance with the following Examples 8 to 11 by incorporating varying amounts of LUDOX SM-30 in the composition, the amount of the water being correspondingly reduced, as previously. In the procedure used for making these toothpastes, however, the silica sol was added at the end of the mixing procedure just prior to final pH adjustment with the benzoic acid. The amounts of the silica sol added are indicated below.

| Example | Amount of Silica Sol added (% by weight of the toothpaste) |
|---|---|
| 8 | 0.1 |
| 9 | 0.5 |
| 10 | 1.0 |
| 11 | 3.0 |

These toothpastes were also stored at 65° C for 1 month. In the case of Example 8 there was no noticeable swelling of the toothpaste tubes and there was only slight swelling in the case of Examples 9 to 11, again demonstrating the inhibitory effect of the silica sol.

What is claimed is:

1. Process for inhibiting the swelling of aluminum toothpaste tubes containing a toothpaste composition comprising from about 20 percent to about 60 percent by weight of an alumina trihydrate having an average particle size of from about 3 to about 30 microns, in which process there is incorporated in the toothpaste composition a silica sol of which the silica particles are negatively charged in an amount of at least about 0.001 percent, calculated as silica by weight of the toothpaste, effective to stabilise the toothpaste against gassing of the aluminum tubes.

2. A process as claimed in claim 1, wherein said silica sol has a silica concentration of from about 5 percent to about 40 percent by weight.

3. A process as claimed in claim 1, wherein said silica sol is incorporated in the toothpaste composition in an amount of from 0.001 percent to about 3 percent calculated as silica by weight of the toothpaste composition.

4. A process as claimed in claim 1, wherein the toothpaste composition has a pH of about 6 to about 8.

* * * * *